United States Patent [19]

Brown et al.

[11] Patent Number: 4,940,543

[45] Date of Patent: * Jul. 10, 1990

[54] PLASMA COLLECTION SET

[75] Inventors: Richard I. Brown, Northbrook; David E. Cerny, Crystal Lake; John T. Foley, Wheeling; Joseph C. West, Jr., Fox Lake, all of Ill.

[73] Assignee: Baxter International Inc., Deerfield, Ill.

[*] Notice: The portion of the term of this patent subsequent to Feb. 21, 2006 has been disclaimed.

[21] Appl. No.: 277,890

[22] Filed: Nov. 30, 1988

Related U.S. Application Data

[63] Continuation of Ser. No. 8,718, Jan. 30, 1987, Pat. No. 4,806,252.

[51] Int. Cl.⁵ .............................................. B01D 21/26
[52] U.S. Cl. ................................ 210/369; 210/380.1; 494/10; 494/18; 494/45
[58] Field of Search ............... 15/17, 345, 447; 604/6; 210/114, 360.1, 369, 370, 371, 380.1, 512.1, 744, 745, 781, 782, 787, 789; 494/10, 18, 37, 45, 60

[56] References Cited

U.S. PATENT DOCUMENTS

| | | | |
|---|---|---|---|
| Re. 29,738 | 8/1978 | Adams | 350/574 |
| 3,655,123 | 4/1972 | Judson et al. | 494/10 |
| 3,708,110 | 1/1973 | Unger et al. | 494/45 |
| 3,724,747 | 4/1973 | Unger et al. | 494/45 |
| 3,737,096 | 6/1973 | Jones et al. | 494/9 |
| 3,987,961 | 10/1976 | Sinn et al. | 494/45 |
| 4,007,871 | 2/1977 | Jones et al. | 210/789 |
| 4,010,894 | 3/1977 | Kellogg et al. | 494/45 |
| 4,056,224 | 11/1977 | Lolachi | 494/18 |
| 4,086,924 | 5/1978 | Latham, Jr. | 604/6 |
| 4,094,461 | 6/1978 | Kellogg et al. | 494/81 |
| 4,108,353 | 8/1978 | Brown | 494/18 |
| 4,109,854 | 8/1978 | Brown | 494/18 |
| 4,109,855 | 8/1978 | Brown et al. | 494/18 |
| 4,164,318 | 8/1979 | Boggs | 494/45 |
| 4,213,561 | 7/1980 | Bayham | 494/45 |
| 4,230,263 | 10/1980 | Westberg | 494/45 |
| 4,245,383 | 1/1981 | Boggs | 29/428 |
| 4,261,507 | 4/1981 | Baumler | 494/45 |
| 4,268,393 | 5/1981 | Persidsky et al. | 210/516 |
| 4,278,202 | 7/1981 | Westberg | 210/927 |
| 4,303,193 | 12/1981 | Latham, Jr. | 604/6 |
| 4,304,357 | 12/1981 | Schoendorfer | 494/21 |
| 4,344,560 | 8/1982 | Iriguchi et al. | 210/787 |
| 4,356,958 | 11/1982 | Kolobow et al. | 494/43 |
| 4,379,452 | 4/1983 | De Vries | 604/6 |
| 4,386,730 | 6/1983 | Mulzet | 494/81 |

(List continued on next page.)

FOREIGN PATENT DOCUMENTS

2002266 2/1979 United Kingdom .

OTHER PUBLICATIONS

WO85/02561, 06/85, PCT Int'l App.

*Primary Examiner*—W. Gary Jones
*Attorney, Agent, or Firm*—Paul C. Flattery; Bradford L. Price; Garrettson Ellis

[57] ABSTRACT

An apparatus and method of separating a component from a collected quantity of fluid. The apparatus includes a dual member centrifuge and an associated fluid flow transfer set. The transfer set has a collection container in which a quantity of fluid can be initially accumulated. The collection container is formed as a disk-shaped plastic member with an elongated generally radially extending barrier member formed therein. A component collection container is in fluid flow communication with the disk-shaped container. The method provides for centrifugation of the collection container in the dual member centrifuge thereby separating out the selected fluid component. The component can then be pumped out of the collection container into the component accumulation container. The residual fluid can be sealed in the collection container for later use. The component collection container can be separated and sealed also for later use.

16 Claims, 4 Drawing Sheets

U.S. PATENT DOCUMENTS

| | | | |
|---|---|---|---|
| 4,387,848 | 6/1983 | Kellogg et al. | 494/43 |
| 4,402,680 | 9/1983 | Schoendorfer | 494/17 |
| 4,405,079 | 9/1983 | Schoendorfer | 494/10 |
| 4,412,831 | 11/1983 | Avery et al. | 494/46 |
| 4,413,771 | 11/1983 | Rohde et al. | 494/17 |
| 4,413,772 | 11/1983 | Rohde et al. | 494/77 |
| 4,413,773 | 11/1983 | Rohde et al. | 494/37 |
| 4,416,654 | 11/1983 | Schoendorfer et al. | 494/10 |
| 4,417,884 | 11/1983 | Schoendorfer et al. | 494/4 |
| 4,419,089 | 12/1983 | Kolobow et al. | 494/45 |
| 4,421,503 | 12/1983 | Latham, Jr. et al. | 494/17 |
| 4,430,072 | 2/1984 | Kellogg et al. | 494/45 |
| 4,439,178 | 3/1984 | Mulzet | 494/18 |
| 4,447,221 | 5/1984 | Mulzet | 494/45 |
| 4,464,167 | 8/1984 | Schoendorfer et al. | 494/10 |
| 4,474,568 | 10/1984 | Schoendorfer et al. | 604/4 |
| 4,482,342 | 11/1984 | Lueptow et al. | 494/21 |
| 4,493,691 | 1/1985 | Calari | 494/10 |
| 4,530,691 | 7/1985 | Brown | 494/45 |
| 4,531,932 | 7/1985 | Luppi et al. | 604/6 |
| 4,617,009 | 10/1986 | Ohlin et al. | 494/21 |
| 4,724,317 | 2/1988 | Brown et al. | 494/10 |
| 4,806,252 | 2/1989 | Brown et al. | 210/744 |

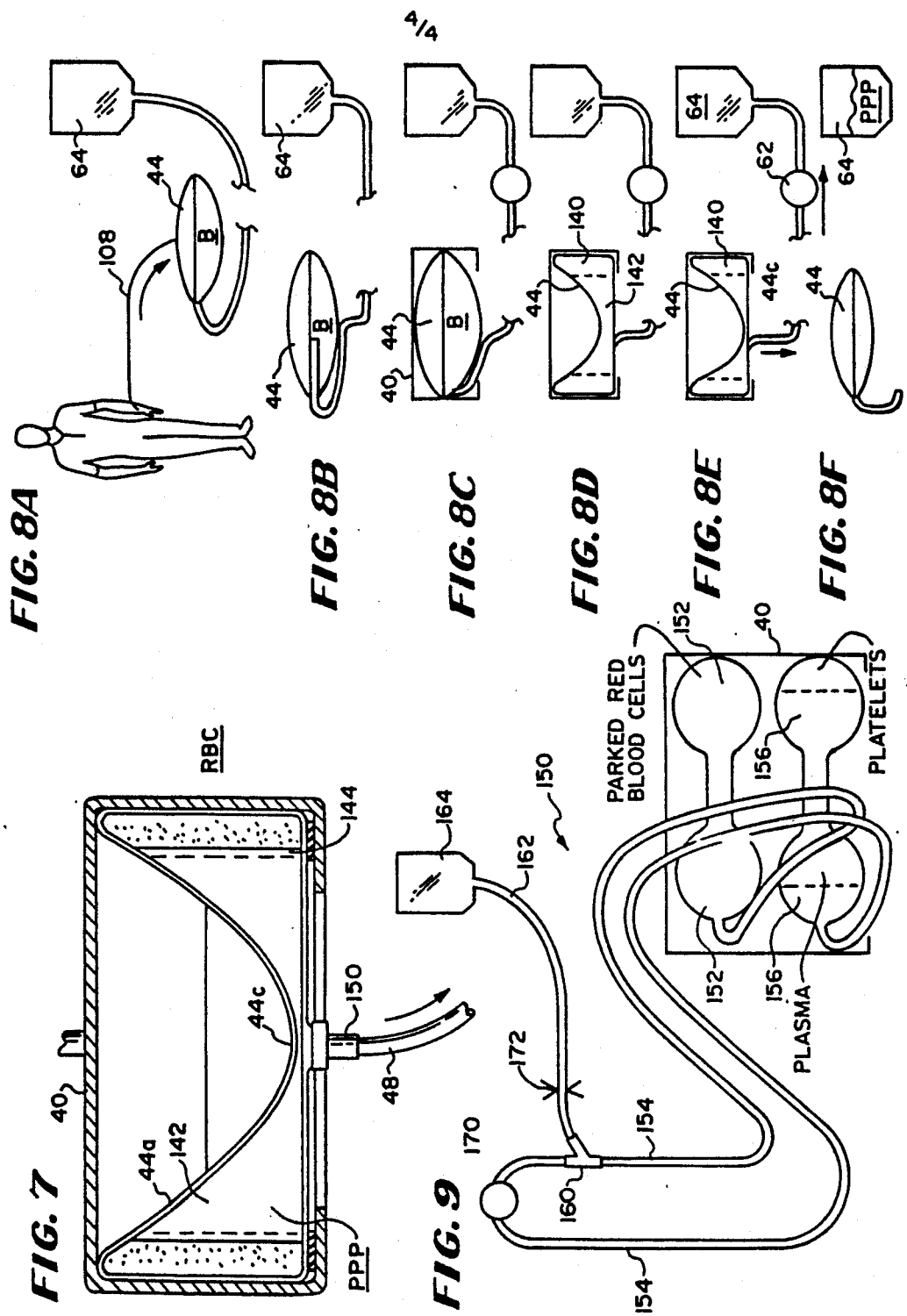

PLASMA COLLECTION SET

This is a continuation, of application Ser. No. 008,718, filed 1/30/87 now U.S. Pat. No. 4,806,252.

TECHNICAL FIELD OF THE INVENTION

The invention pertains to the field of plasma collection. More particularly, the invention pertains to the collection of plasma from volunteer donors at temporary sites, remote from medical facilities, with portable lightweight equipment capable of easy transport.

BACKGROUND OF THE INVENTION

The collection of blood from volunteer donors has become a very successful and very refined activity. The development of single needle, single use, disposable blood collection sets has provided a safe, relatively inexpensive and donor comfortable medium for use in the blood collection process. Such sets have made possible large-scale collection of blood from volunteer donors at sites such as church halls, schools or offices which might be remote from medical facilities. The availability of volunteer donors is important in that such donors tend to be relatively healthy. In addition, they provide a potentially much larger reservoir of donatable blood than is available from the available group of paid donors.

In recent years, the processing of whole blood collected from donors has come to routinely include separating the blood into therapeutic components. These components include red blood cells, platelets and plasma. Various techniques and apparatus have been developed to facilitate the collection of whole blood and the subsequent separation of therapeutic components therefrom.

The collection of plasma from volunteer donors, as opposed to the collection of whole blood, has not been nearly as successful. As a result, much of the plasma now collected comes from paid donors, as opposed to volunteer donors. It would be very desirable to be able to upgrade the collection of plasma so that it becomes a volunteer based activity to a much greater extent than it is currently.

One consideration in the collection and processing of whole blood is the requirement that the collecting and the processing take place under sterile conditions. A second consideration involves the requirement that processing take place under conditions that maximize the storage life of the blood components. Unless the processing takes place within a single sealed system, the permitted storage duration and usable lifetime of the blood components is substantially shortened. Components processed within a sealed system can be stored for four to six weeks or longer before use. On the other hand, whole blood or components thereof must be used within 24 hours if the system seal is broken.

One form of processing of whole blood into various therapeutic components includes centrifuging the blood so as to bring about the desired separation of those components.

To promote the desired ends of sterile processing within a single sealed system, dual member centrifuges can be used. One example of this type of centrifuge is disclosed in U.S. Pat. No. Re. 29,738 to Adams entitled "Apparatus for Providing Energy Communication Between a Moving and a Stationary Terminal." As is now well known, due to the characteristics of such dual member centrifuges, it is possible to rotate a container containing a fluid, such as a unit of donated blood, and to withdraw a separated fluid component, such as plasma, into a stationary container, outside of the centrifuge without using rotating seals. Such container systems can be formed as closed, sterile transfer sets.

The Adams patent discloses a centrifuge having an outer rotatable member and an inner rotatable member. The inner member is positioned within and rotatably supported by the outer member.

The outer member rotates at one rotational velocity, usually called one omega, and the inner rotatable member rotates at twice the rotational velocity of the outer housing or two omega. There is thus a one omega difference in rotational speed of the two members. For purposes of this document, the term "dual member centrifuge" shall refer to centrifuges of the Adams type.

The dual member centrifuge of the Adams patent is particularly advantageous in that, as noted above no seals are needed between the container of fluid being rotated and the non-moving component collection container. The system of the Adams patent, provides a way to process blood into components in a single, sealed, sterile system wherein whole blood from a donor can be infused into the centrifuge while the two members of the centrifuge are being rotated.

An alternate to the apparatus of the Adams patent is illustrated in U.S. Pat. No. 4,056,224 to Lolachi entitled "Flow System for Centrifugal Liquid Processing Apparatus." The system of the Lolachi patent includes a dual member centrifuge of the Adams type. The outer member of the Lolachi centrifuge is rotated by a single electric motor which is coupled to the internal rotatable housing by belts and shafts.

U.S. Pat. No. 4,108,353 to Brown entitled "Centrifugal Apparatus With Oppositely Positioned Rotational Support Means" discloses a centrifuge structure of the Adams type which includes two separate electrical motors. One electric motor is coupled by a belt to the outer member and rotates the outer member at a desired nominal rotational velocity. The second motor is carried within the rotating exterior member and rotates the inner member at the desired higher velocity, twice that of the exterior member.

U.S. Pat. No. 4,109,855 to Brown et al. entitled "Drive System For Centrifugal Processing Apparatus" discloses yet another drive system. The system of the Brown et al. patent has an outer shaft, affixed to the outer member for rotating the outer member at a selected velocity. An inner shaft, coaxial with the outer shaft, is coupled to the inner member. The inner shaft rotates the inner member at twice the rotational velocity as the outer member. A similar system is disclosed in U. S. Pat. No. 4,109,854 to Brown entitled "Centrifugal Apparatus With Outer Enclosure".

Centrifuges of the type disclosed in the above indentified Brown et al. and Brown patents can be utilized in combination with a sealed fluid flow transfer set of the type disclosed in U.S. Pat. No. 4,379,452 to DeVries. The disclosure of the DeVries patent is incorporated herein by reference. The set of the DeVries patent incorporates a blood collection container that has a somewhat rectangular shape similar to those of standard blood collection sets. One embodiment of this combined system is the CS3000 cell separator system marketed by Travenol Laboratories, Inc.

The CS3000 incorporates a dual member centrifuge in combination with a sealed set of the type disclosed in DeVries. This is a continuous pheresis system that requires the donor to receive two needle punctures. Such systems have been extensively used in blood centers for plasma and platelet pheresis.

The CS3000 is a large and expensive unit that is not intended to be portable. Further, the DeVries type transfer sets are quite complex to install and use. They are also an order of magnitude more expensive than a standard, multi-container blood collection set.

A further alternate to the Adams structure is illustrated in U.S. Pat. No. 4,530,691 to Brown entitled "Centrifuge With Movable Mandrel." The specification and figures of this Brown patent are hereby incorporated by reference herein. The centrifuge of this latter Brown patent also is of the Adams-type. However, this latter centrifuge has an exterior member which is hinged for easy opening. When the hinged upper section is pivoted away from the bottom section, it carries the rotatable inner member along with it.

The inner member supports a receiving chamber with a spring biased mandrel which continually presses against a sealed, blood containing, container positioned within the receiving chamber. The system of this latter Brown patent also discloses the use of two separate electric motors to rotate the inner and outer members. The motors are coupled to a control system.

Another continuous centrifuge based system is disclosed in Judson et al. U.S. Pat. No. 3,655,123 entitled "Continuous Flow Blood Separator." The system of the Judson et al. patent uses two needles, an outflow needle and an inflow needle. Whole blood is drawn from a donor via the outflow needle. The whole blood fills a buffer bag. Blood from the buffer bag drains, under the force of gravity into a centrifuge. The system of the Judson et al. patent uses the centrifuge to separate blood components. The plasma can be collected in a container. The red blood cells can be returned to the donor via the inflow needle. The system of the Judson et al. patent does not use a dual member centrifuge. The system of the Judson et al. patent does not appear to be readily portable.

There thus continues to be a need for a method and related apparatus of plasmapheresis which can readily be used with volunteer donors at various temporary locations. This method and related apparatus should be usable by technicians with a level of skill commensurate with the level of skill now found at volunteer-based blood collection centers. Further, both the method and related apparatus should be readily portable to locations such as churches or schools where blood collection centers are temporarily established. Preferably the apparatus will be essentially self-contained. Preferably, the equipment needed to practice the method will be relatively inexpensive and the blood contacting set will be disposable each time the plasma has been collected from a single donor.

SUMMARY OF THE INVENTION

In accordance with the invention, a fluid collection set is provided which is useable in the collection of a quantity of fluid. The set is positionable in part in a receiving chamber of a centrifuge. By centrifugation, a selected fluid component can be separated from the fluid in the set.

The set includes a flexible disk-shaped collection container. This container can be used to accumulate a quantity of fluid. The container can have an elliptical or a circular periphery. A barrier member is positioned within the container to impede the movement of the fluid within the container during the centrifugation process.

A blood drawing cannula can be coupled to the container by a draw conduit. The cannula can be used to pierce the vein of a donor for the purpose of filling the container with a unit of whole blood.

A fluid flow conduit, such as a section of hollow tubing is attached at one end to the disk-shaped collection container. The second end of the conduit is attached to a second container in which the separated component is to be accumulated. The separated component container is positionable outside of the centrifuge, at a fixed location, while the collection container is rotated within the receiving chamber of the centrifuge.

In one embodiment of the invention, the barrier member can be formed as an elongated generally extending radial member. The collection container can be formed of first and second planar plastic members which are joined, perhaps by heat sealing, along the curved periphery.

The fluid can be for example, whole blood collected from a donor. In this embodiment, the blood collection container is positioned in the receiving chamber of the dual member centrifuge. The separated component can be, for example, plasma. Subsequent to rotating the collection container in the centrifuge, the separated plasma can be pumped into a plasma collection container exterior to the centrifuge.

A method of practicing the invention includes providing a dual member centrifuge. In addition, a sealed fluid collection system can be provided. The fluid collection system has a disk-shaped fluid collection container. The fluid collection container is filled with a quantity of fluid and then is positioned within a receiving chamber of the centrifuge.

The collection container is rotated at a predetermined rotational velocity which results in the separation of the selected component from the remaining fluid in the container. During the separating step, the separated fluid fills an inner annular region within the disk-shaped container. An outer annular region, adjacent the interior peripheral wall of the receiving chamber is filled with the residual fluid in the container. A central region of the container is emptied of fluid during the centrifugation process and collapses. As a result, the container assumes a donut or toroidal shape.

The separated fluid component can then be withdrawn from the container. The withdrawing step can include pumping the separated component from the collection container into a component container.

In a preferred embodiment of the invention, the disk-shaped container is rotated at a relatively high speed, on the order of 4,000 rpm for 7-10 minutes to effect the separation. The container is then slowed during a 2 to 4 minute period to about 1,000 rpm for the purpose of withdrawing the separated component. During the slow-down process the generally radially extending barrier member within the container blocks movement or sliding of the fluid in the container with respect thereto.

In yet another embodiment, first and second components can be separated. The first and second separated components separate from the residual fluid in a two stage process. Initially, both separated components are mixed together. Over a period of time, as the receiving chamber continues to rotate, the two separated components will in turn separate from each other.

The system of the present invention is particularly advantageous in that the donor experiences only a single needle puncture as is the case when donating blood. Further, once the unit of blood has been drawn, the donor is finished and can leave. Finally, the transfer set should have a cost comparable to the cost of currently available blood collection sets.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 7 is an enlarged view, partly in section of an alternate structure also illustrating separation of a component from a fluid in accordance with the present invention;

FIG. 8 illustrates schematically the steps of a method of separating a fluid component in accordance with the present invention; and FIG. 9 is an overall schematic view of an alternate fluid flow transfer set and method of separating first and second fluid components in accordance with the present invention.

DETAILED DESCRIPTION OF THE PREFERRED EMBODIMENT

Figure 1:
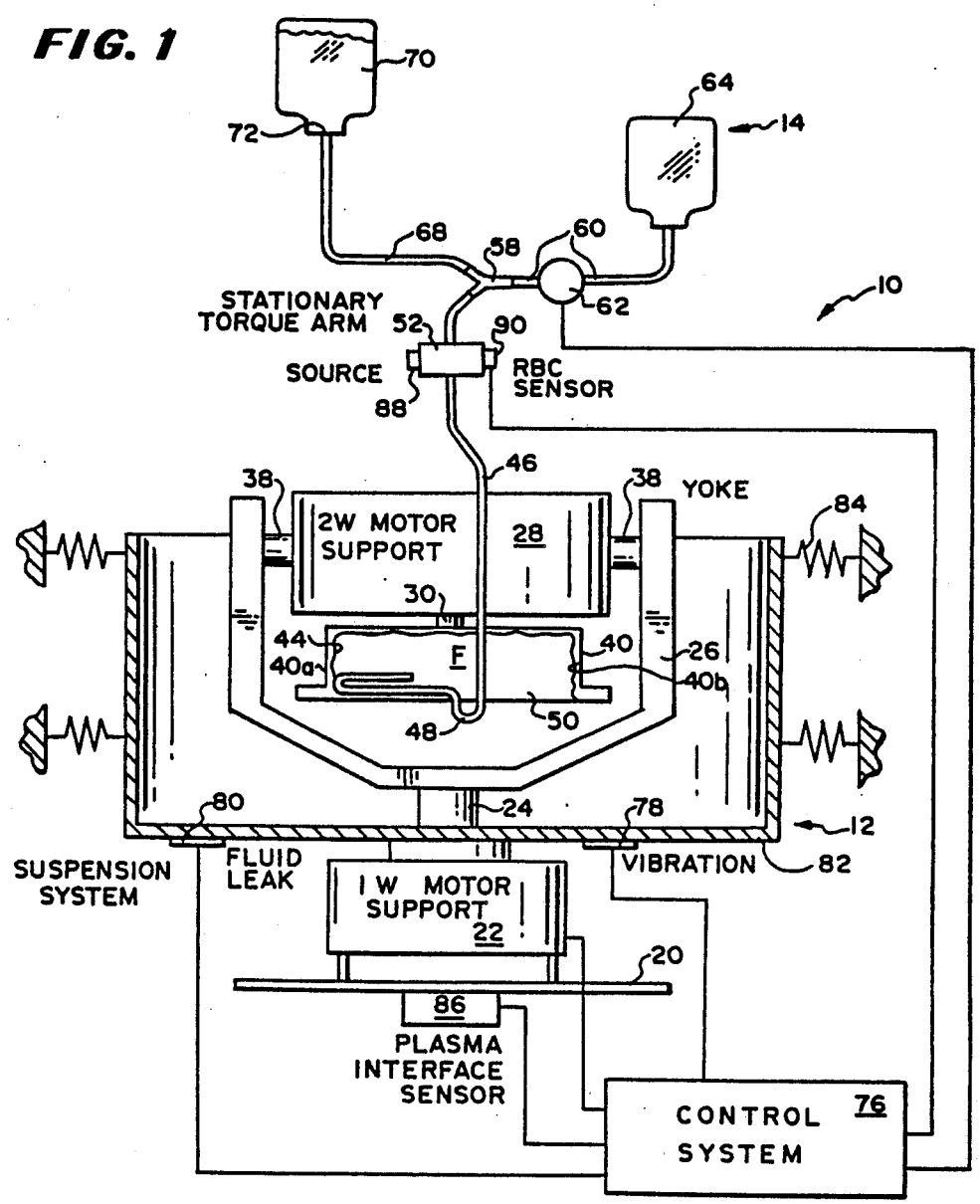
FIG. 1 is an overall system view schematically illustrating a readily transportable dual member centrifuge and fluid flow transfer set in accordance with the present invention.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates a readily transportable system 10 in accordance with the present invention. The system 10 includes a relatively light-weight dual member centrifuge 12 and an associated fluid flow transfer set 14.

The dual member centrifuge 12 is of the Adams type having a stationary support 20 on which is mounted a first motor 22. The first motor 22 has a rotary output shaft 24 which rotates at a first angular velocity conventionally referred to as one omega. Fixedly attached to the rotary shaft 24 is a yoke 26. The yoke 26 supports a second electric motor 28. The electric motor 28 has a rotary output shaft 30. The shaft 30 rotates at an angular velocity twice that of the shaft 24, conventionally referred to as two omega. The motor 28 is pivotably attached to the yoke 26 at pivot points 36 and 38.

Affixed to the rotating shaft 30 is a cylindrical receiving chamber 40. The receiving chamber 40 is rotated by the shaft 30. The chamber 40 has a cylindrical exterior peripheral surface 40a as well as a cylindrical interior peripheral surface 40b. The chamber 40 supports and rotates a collection container 44. The chamber 40 has an inner diameter on the order of six inches and an internal length on the order of two inches.

The collection container 44 is in fluid flow communication via a flexible conduit 46 with the remainder of the set 14. A proximal end 48 of the flexible fluid flow conduit 46 extends into the interior volume 50 of the container 44. The container 40 can be filled with a quantity of fluid such as whole blood provided by a donor.

The fluid flow conduit 46 is supported by a stationary torque arm 52. The use of such torque arms is well known to those skilled in the art with respect to dual member centrifuges of the Adams type. A distal end 54 of the fluid flow conduit 46 is coupled to a "y" junction member 58. A branch conduit 60 coupled to the junction member 58 is physically coupled to a separated component pump 62. The separated component could, for example, be plasma and the pump 62 could be a plasma pump. The fluid flow conduit 60 is also in fluid flow communication with a separated component collection container 64. The container 64 could be a standard plasma collection container.

Also coupled to the junction member 58 is a third fluid flow conduit 68. The fluid flow conduit 68 is coupled to a red cell nutrient and preservative solution container 70. The solution in the container 70 is of a known type which provides nutrients to packed red blood cells subsequent to the plasma pheresis process. Contents of such solutions include dextrose, sodium chloride, mannitol and adenine. One appropriate solution is marketed by Travenol Laboratories, Inc. under the trademark ADSOL. The container 70 is sealed with a frangible member 72 which can be broken at an appropriate point in the plasma pheresis process.

The system 10 also includes a control system 76 which is coupled to the motors 22 and 28. The control system 76 receives feedback from vibration and fluid leak sensors 78 and 80. The sensors 78 and 80 are fixedly supported by a stationary suspension system 82. The system 82 can be connected to resilient members 84 to stabilize the centrifuge 12 during operation.

In addition, if desired, a plasma interface sensor 86 can be provided which is in turn coupled to the control system 76. The plasma interface sensor 86 can be used to detect the location of the interface between the separated plasma and packed red blood cells in the container 44 during the centrifugation process. An appropriate interface is disclosed in co-pending U.S. patent application Ser. No. 805,512 entitled OPTICAL DATA COLLECTION APPARATUS AND METHOD filed Dec. 5, 1985 and assigned to the assignee of the present invention. The disclosure of that co-pending application is incorporated herein by reference.

As an alternate, the dual member centrifuge 12 can sense the presence of the plasma/red blood cell interface in the tubing member 46 to 60. For example, a source of radiant energy 88 could be attached to the stationary torque arm 52. A sensing member 90 can also attach to the stationary torque arm 52 displaced from the source 88. The conduit 46 extends between the source 88 and the sensor 90. The sensor 90 detects a plasma and packed red blood cell interface in the flexible conduit 46 and the plasma in being pumped off by the pump 62. A signal from the red blood cell sensor 90 indicating that the interface has been detected is also coupled to the control system 76 and can terminate the plasma pheresis operation.

The source 88 and sensor 90 can also be positioned adjacent the tubing member 60.

Figure 2:
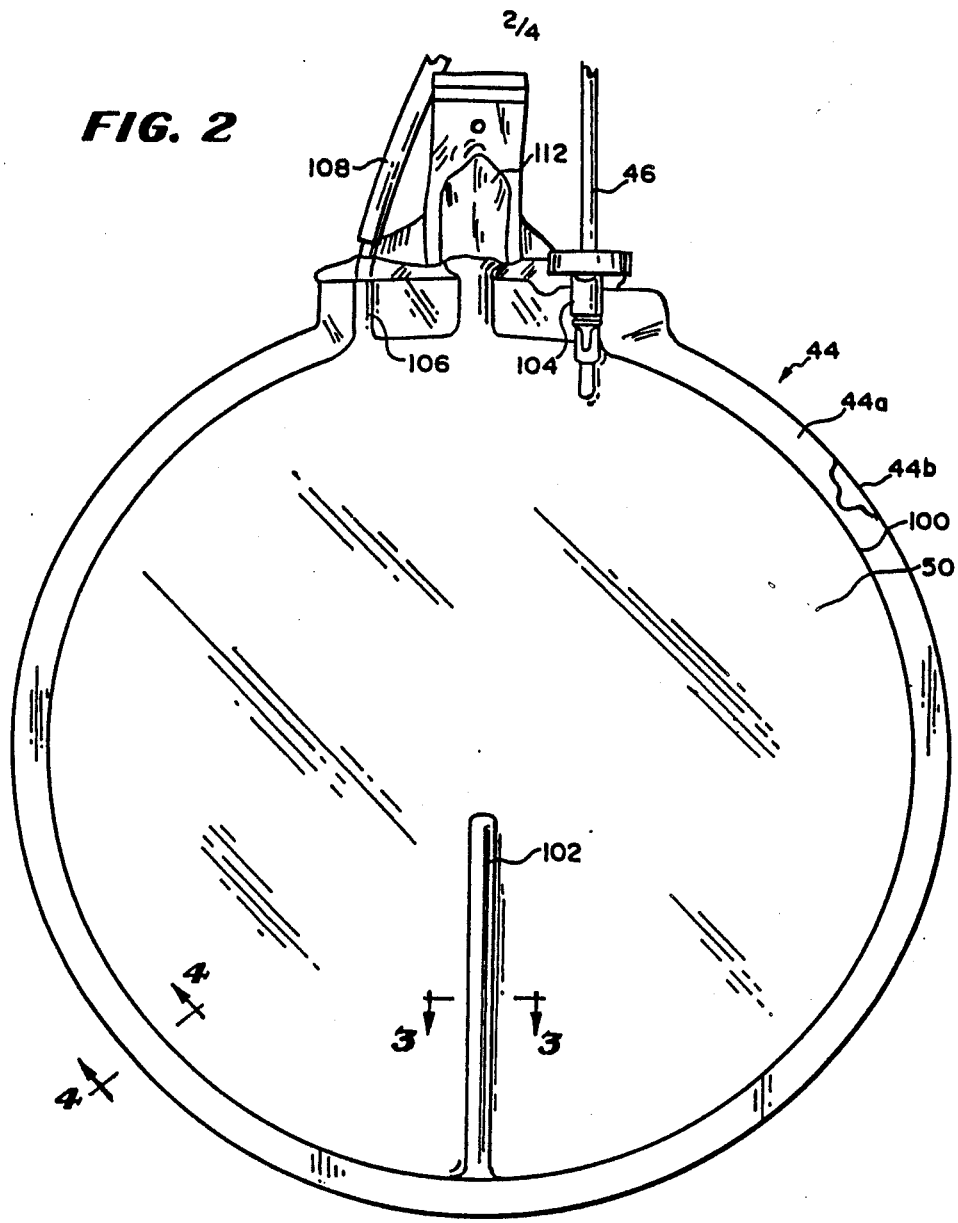
FIG. 2 is a top plan view of a blood collection container in accordance with the present invention.
Figure 3:
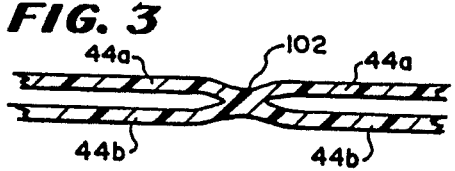
FIG. 3 is a view in section taken along plane 3—3 of FIG. 2 illustrating the relationship of the radially extending barrier member to the sheet members of the container.
Figure 4:
FIG. 4 is a view in section taken along plane 4—4 of FIG. 2 illustrating the relationship between the container forming sheet members and the circular peripheral seal of the container.

FIGS. 2–4 illustrate the structure of the collection container 44. The collection container 44 is disk-shaped and can be formed of first and second plastic sheet members 44a and 44b. Plastic sheets of the type normally used for blood collection of sets are useable to form the container 44. The first and second plastic members 44a and 44b can be heat sealed together at a circular periphery 100. The sealing of the circular periphery 100 can be brought about by radio frequency heat sealing or by means of heated platens. Within the circular periphery 100 is defined the interior collection volume 50. The length of the diameter of the circular periphery 100 is on the order of 7 to 8 inches.

It will be understood, that while an essentially circular container 44 is illustrated in FIG. 2, the present invention is not limited to circular containers. It will be understood that a disk-shaped container could also include a container with an elliptically shaped sealed periphery.

The container 44 includes an elongated, generally radially extending barrier member 102 which extends into the interior region 50. The barrier member 102 is formed by heat sealing together a region of the sheet members 44a and 44b.

The container 44 includes a port 104 which is in fluid flow communication with the flexible fluid flow conduit 46. The container 44 also includes a port 106. The port 106 is a filling port used during the draw cycle when the donor is bleeding into and filling the container 44. The port 106 is also in fluid flow communication with a fluid flow conduit 108. A distal end of the fluid flow conduit 108 can be connected to a draw cannula 110 intended to be inserted into the vein of the donor.

The container 44 also includes a dispensing port 112. The port 112 is closed with a pierceable member and can be used to subsequently dispense the remaining contents in the container 44 once the pheresis process has been completed.

FIGS. 3 and 4 illustrate in section the relationship between the barrier member 102 and the sheet members 44a and 44b as well as the curved peripheral seal 100 and the sheet members 44a and 44b.

Figure 5:
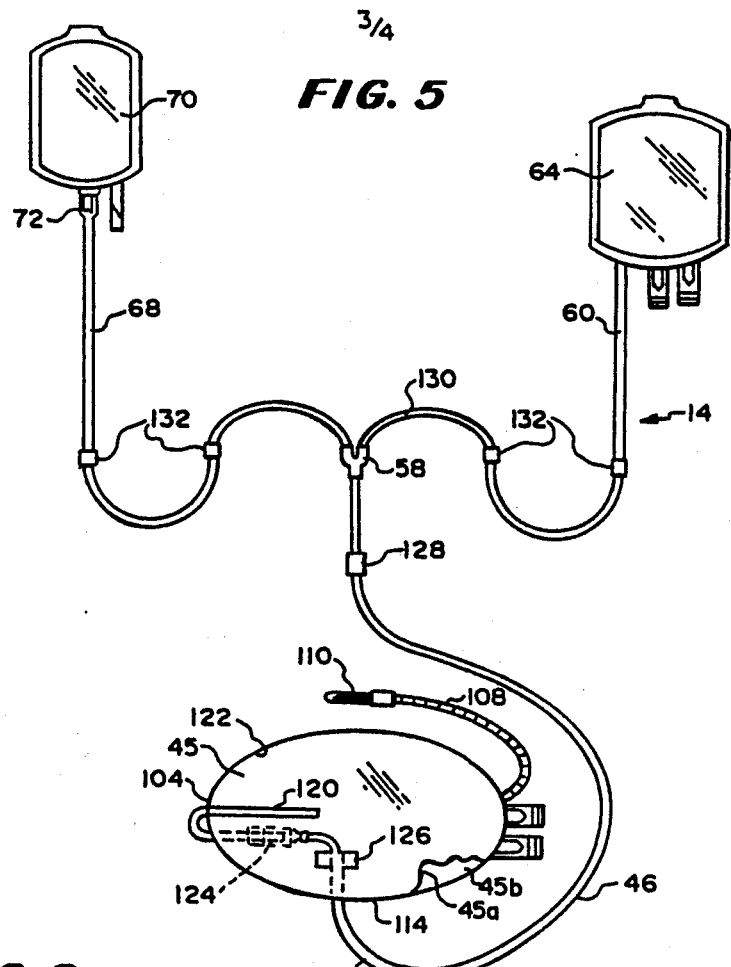
FIG. 5 is a schematic view illustrating an alternate fluid flow transfer set in accordance with the present invention.

FIG. 5 illustrates an overall view of the fluid flow transfer set 14. The transfer set 14 can be used to accumulate a unit of donated blood by the same blood collection technicians as now use standard blood collection sets. Further, the cost of the set 14 should be comparable to the cost of current blood collection sets.

In the embodiment of FIG. 5, the circular container 44 has been replaced by an elliptical disk-shaped container 45. The container 45 includes the draw port 106 which is in fluid flow communication with the draw conduit 108. The draw conduit 108 terminates at its free end in the cannula 110. The container 45 can be formed in the same manner as the container 44 by heat sealing the planar sheet members 45a and 45b along the elliptical periphery 114.

The container 45 also includes the port 104 which is formed in the elliptically shaped peripheral wall 114. The proximal end 48 of the fluid flow conduit 46 extends through the port 104 and terminates in a section 120 in the interior volume 122 defined by the container 45. The section 120 is formed of a hollow tubing member which is in fluid flow communication with the proximal end 48. In addition, the section 120 is sealingly attached to adjacent regions of the plastic sheet members 45a and 45b. The sealingly attached member 120 thus forms an inwardly extending, elongated barrier analogous to the barrier 102 in the container 44. The proximal end 48 is sealed by a breakable cannula member 124 until the draw cycle has been completed. The proximal end 48 can be fixedly attached to the exterior of the sheet member 45b at a supporting weld 126.

A bushing 128 can be provided to slideably engage the stationary torque arm 52 to prevent abrasion and wearing of the conduit 46 during the centrifugation process. In addition, the source of radiant energy 88 and respective sensor 90 could be positioned adjacent a transparent region 130 of the tubing member 60 for the purpose of sensing the plasma/packed red blood cell interface at the end of the pheresis process. Pump segment keepers 132 can also be provided to restrain tubing members 60 and 68 in position with respect to pumps such as the plasma pump 62 which could for example be a peristaltic pump.

Figure 6:
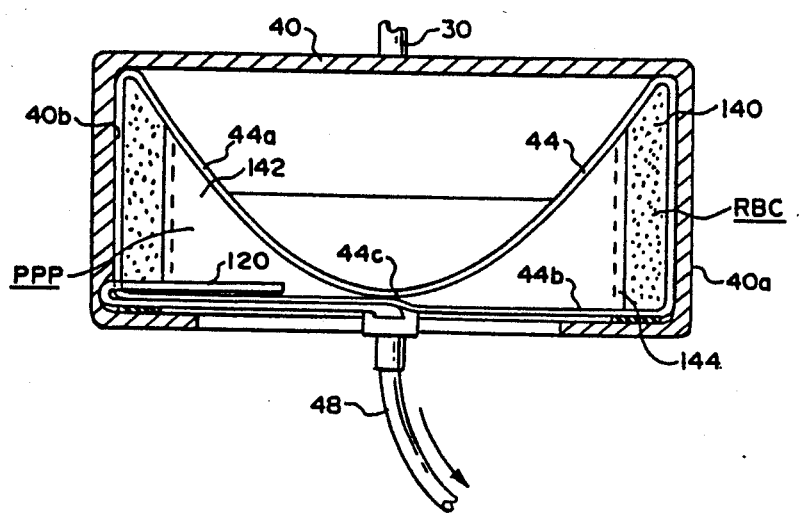
FIG. 6 is a enlarged view, partly in section, of the receiving chamber of the centrifuge of FIG. 1 illustrating separation of a component from a fluid in accordance with the present invention.

FIG. 6 illustrates the system 10, and more particularly the receiving chamber 40 with fluid filled container 44 therein partway through the centrifugation process. The centrifugation process takes on the order of 7–10 minutes at a speed of about 4,000 rpm. During this time, the whole blood in the container 44 is essentially separated into two major components.

The heavier red blood cells accumulate in an exterior annular region 140 adjacent the interior peripheral wall 40b. Platelet poor plasma collects in an interior annular region 142 as the plasma is not as heavy as the red blood cells. An interface region 144 develops between the exterior toroidal region 140 filled with packed red blood cells and the interior toroidal region filled with platelet poor plasma.

During the high speed separation interval, when the red blood cells are being forced into the outer annular region 140, a central portion 44c of the sheet member 44a is emptied of fluid. As a result, that region collapses, as illustrated in FIG. 6, due to the effects of centrifugal forces generated by rotation of the fluid.

After the 7–10 minute centrifugation interval has passed, the chamber 40 can be slowed to about 1,000 rpm over a 2–4 minute interval. It has been found that the barrier 102 is important during the slow-down period to keep the fluid within the container from sliding and remixing again. By means of the barrier member 102, the fluid is also forced to slow down at the same rate as is the receiving chamber 40. During the slow-down period, the packed red blood cells stay in the annular region 140 and the platelet poor plasma tends to remain in the interior annular region 142.

Once the slow-down interval has passed, the platelet poor plasma can be withdrawn from the region 142 via the fluid flow conduit segment 120. The segment 120 extends into the region 142 through the seal 100. The member 120 in addition to being able to function as the barrier member as discussed above, must extend far enough into the container 44 so as to be located in the region 142 of platelet poor plasma.

It should be noted that the interface 144 could contain platelets which might be drawn off subsequently after the platelet poor plasma in the region 142 has been removed. The peristalic pump 62 can then pump the platelet poor plasma from the region 142 into the container 64.

As the platelet poor plasma is withdrawn from the region 142, the bag 44 will collapse further. The collapsed region 44c will extend toward the interior peripheral wall 40b.

FIG. 7 illustrates an alternate construction of the container 44. The proximal end 48 of the tubing member 46 is coupled to a plasma withdrawal port 150 which is centrally located. In the embodiment of FIG. 7, the container illustrated therein will require a separate elongated radially extending barrier member as in FIG. 2. Except for the location of the plasma withdrawal port 150, the container of FIG. 7 functions essentially the same way as does the container of FIG. 6.

FIG. 8 illustrates a batch method of collecting platelet poor plasma in accordance with the present invention. The method of FIG. 8 is suitable for use in connection with volunteer blood donation programs. The dual housing centrifuge 12 will be relatively lightweight and is easily transportable. Hence, it can be taken to the device locations such as church basements and recreation halls where blood donation programs are temporarily set up.

In FIG. 8a, a donor is illustrated donating a unit of blood B which is accumulated in the bag 44. The bag 44 is intergally attached to the remainder of the set including the plasma collection container 64. As far as the donor is concerned, this is merely a standard blood donation process. Once the unit of blood has been accumulated, the donor is free to leave.

In FIG. 8b the container 44 contains a unit of whole blood B and has been uncoupled from the donor. The draw conduit 108 has been sealed, for instance, by heat sealing. The frangible cannula 124 has been broken so as to place the container 44 into fluid flow communication with the plasma accumulation container 64. FIG. 8c illustrates the blood filled container 44 positioned in the receiving chamber 40 prior to the initiation of centrifugation.

FIG. 8d illustrates the container 44 partway through the centrifugation process. In FIG. 8d the red blood cells have started to fall way from the plasma into the annular region 140. The platelet poor plasma is starting to accumulate in the inner annular region 142.

FIG. 8e illustrates the container 44 subsequent to the slow down step and while platelet poor plasma is being withdrawn from the region 142 by means of the pump 62. The accumulated platelet poor plasma is being collected in the container 64. As is illustrated in FIG. 8e, the central region 44c of the container 44 is collapsing.

FIG. 8f illustrates the container 44 from which the platelet poor plasma has been removed or withdrawn and after the nutrient mixture in the container 70 has been infused therein. The nutrient mixture prolongs the life of the packed red blood cells and provides a diluting fluid to restore the hematocrit to levels such that the concentrated red blood cells can then be infused into a patient. Also in FIG. 8f, the container 64 of platelet poor plasma is illustrated sealed off and separated from the container 44.

In addition to being able to accumulated platelet poor plasma in a collection container such as the container 64 it is also possible, using another embodiment, to accumulate the platelets in a separate container. FIG. 9 illustrates a fluid flow transfer set 150, related apparatus and method usable for this purpose.

The transfer set 150 includes a first, disk-shaped container 152 such as the container 44 of FIG. 2. The container 152 is in fluid flow communication via a conduit 154 with a second disk-shaped container 156. The container 156 can also have a structure which corresponds to the container 44.

A "y" junction member 160 located in the fluid flow conduit 154 provides a fluid flow path, via a conduit 162, to a container 164. Initially the container 164 contains nutritive solution of the type noted previously with respect to the container 70.

The container 152 is initially filled with whole blood as illustrated in FIG. 8a previously discussed. The set 150 is then mounted on a dual member centrifuge such as the centrifuge 12. The collection container 152 and the second container 156 are both loaded into the receiving chamber 40. The conduit 154 is brought out of the receiving chamber to a stationary region outside of the centrifuge 12 and coupled to a pump 170.

The tubing member 162 is initially clamped shut. The receiving chamber 40 is first rotated at about 3000 rpm for about 5 minutes to separate the red blood cells in the container 152 from the platelet rich plasma. The receiving chamber is then slowed down to 1,000 rpm and the platelet rich plasma is pumped out of the container 152, via the conduit 154 by the pump 170 and into the second container 156.

The rotational velocity of the receiving chamber is then increased to about 4,000 rpm to separate the platelets from the plasma in the container 156. Once the platelets and the plasma have been separated, the plasma forms an annularly shaped region within the container 156 and the platelets form an adjacent exterior annular region surrounding the annular region of platelet poor plasma.

The clamp 172 can then be opened. The nutrient solution can be drained from the container 164 into the packed red blood cells in the container 152. The platelet poor plasma can then be pumped out of the second container 156, via the conduit 154, and into the now empty container 164.

At this time the centrifugation process can be terminated. The three containers 152, 156 and 164 can be removed from the centrifuge 12. The container 152 can be sealed with its contents being the concentrated red blood cells with the nutritive solution added thereto. The container 156 can be sealed with its contents being the platelets remaining therein. Finally, the container 164 can be sealed with its contents being the platelet poor plasma.

With respect to the embodiments of FIGS. 6 and 7, it will be understood that the port to the fluid flow conduit 48 is to be located in the region of platelet poor plasma to effect withdrawal of that separated component from the disk-shaped collection container 44. It will also be understood that the particular advantage of the disk-shaped container is that it provides for self balancing of the rotating collection chamber 40. This is a particularly important feature in that if the collected fluid F in the container 44 is distributed in such a way that the rotating chamber 40 is unbalanced, this will cause unnecessary wear and shorten the life of the apparatus.

Further, it will be understood that while the set 14 has been illustrated in combination with a dual member centrifuge 12, the invention can be practiced without the use of a dual member centrifuge. For example, the entire set 14 could be positioned in the rotary chamber 40. The chamber 40 could be rotated using just a single motor. In this embodiment, a plasma pump such as the parastolic pump 62 could also be located in the rotating chamber 40. The separated platelet poor plasma could be pumped into the plasma collection container 64 after centrifugation has occurred. Alternately, springs could be used to force the separated plasma into a collection container. The particular advantages of the disk-shaped collection chamber 44 will still be realized with these embodiments.

Further, it will be understood that the barrier member, such as the radially extending barrier member 102 of the container 44 provides for enhanced performance of the system. However, the container 44 could be formed as a disk-shaped container without that barrier member. In this event, the separated component could be kept from remixing with the residual fluid component in the container by slowing the rotating chamber 40 down very slowly. This will result in the separated component fluid and the residual fluid tending not to slide within the container causing remixing.

Alternately, instead of an integrally formed barrier such as the barrier member 102, a barrier means can be formed by providing the rotating chamber with clamping means. The clamping means can be provided to clamp the two sheet members 44a and 44b together in a radially extending region so as to create a barrier member which is effective to inhibit remixing within the container 44 but which is formed external to that container.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A fluid collection set, usable in the collection of a quantity of fluid, and positionable in part in a receiving chamber of a centrifuge for the purpose of separating, by centrifugation, a selected fluid component, the set comprising:
    a flexible, disk-shaped collection container defining an interior collection volume in which a quantity of fluid can be collected with said collection container having a circular, sealed periphery, and a generally radial container wall heat seal line extending from said periphery toward a center thereof, thereby blocking circumferential fluid flow along said periphery;
    a fluid flow contact with a proximal end and a distal end, said proximal end in fluid flow communication with said interior collection volume;
    a separated component container in fluid flow communication with said distal end of said conduit with said disk-shaped collection container rotatable in the receiving chamber while simultaneously coupled to said component container so as to accumulate the component separated from the quantity of fluid rotated in the receiving chamber.

2. A set as in claim 1 with said collection container formed of first and second planar plastic members sealingly joined along said circular periphery.

3. A set as in claim 2 with said conduit formed as a flexible tubular member.

4. A set as in claim 2 including a second separated component container in fluid flow communication with said collection container.

5. A set as in claim 4 including means for filling said collection container.

6. A set as in claim 1 wherein the centrifuge is a dual member centrifuge.

7. A set as in claim 6 with said separated component container positionable, fixedly located outside of the centrifuge.

8. A set as in claim 7 with said generally radially extending heat seal line formed as a radially extending sealed region between first and second planar plastic members.

9. A set as in claim 1 wherein said proximal end of said fluid flow conduit is located in a region of said collection volume which will contain only the separated fluid component after centrifugation has taken place.

10. A fluid collection set, usable in the collection of a quantity of whole blood, and positionable in part in a receiving chamber of a centrifuge for the purpose of separating, by centrifugation, a selected blood component, the set comprising:
    a flexible, plastic, disk-shaped collection container defining an interior collection volume in which a quantity of whole blood from a donor can be collected with said collection container having a circular periphery with first and second opposed walls of said container sealed together with a generally radial heat seal line extending from a region of said circular periphery toward a center thereof to form a barrier to circumferential flow adjacent said periphery;
    a fluid flow circuit with a proximal end and a distal end, said proximal end in fluid flow communication with said interior collection volume;
    a separated component container in fluid flow communication with said distal end of said conduit with said disk-shaped collection container rotatable in the receiving chamber while simultaneously coupled to said component container so as to accumulate the component separated from the quantity of blood rotated in the receiving chamber.

11. A set as in claim 10 with said collection chamber formed of first and second planar plastic members sealingly joined along said circular periphery.

12. A set as in claim 11 with said proximal end of said fluid flow conduit extending into said collection chamber through a selected region of said curved periphery.

13. A set as in claim 12 with said proximal end extending into a region of said collection container containing essentially only the separated component after centrifugation has taken place.

14. A set as in claim 11 including a second separated component container in fluid flow communication with said collection container.

15. A set as in claim 14 including means for filling said disk-shaped collection container with the quantity of whole blood.

16. A set as in claim 14 wherein the centrifuge is a dual member centrifuge and with said proximal end of said fluid flow conduit essentially non-rotatable with respect to said distal end.

* * * * *

UNITED STATES PATENT AND TRADEMARK OFFICE
CERTIFICATE OF CORRECTION

PATENT NO. : 4,940,543
DATED : July 10, 1990
INVENTOR(S) : Richard I. Brown, et al.

It is certified that error appears in the above-identified patent and that said Letters Patent is hereby corrected as shown below:

In claim 1, at column 11, line 59, delete "contact" and substitute - -conduit- - therefor.

In claim 11, at column 12, line 49, delete "chamber" and substitute - - container - - therefor.

In claim 12, at column 12, spanning lines 53 and 54, delete "chamber" and substitute - - container - - therefor.

Signed and Sealed this

Twenty-seventh Day of August, 1991

Attest:

HARRY F. MANBECK, JR.

*Attesting Officer*

*Commissioner of Patents and Trademarks*